US00PP27714P3

(12) United States Plant Patent
Olesen et al.

(10) Patent No.: US PP27,714 P3
(45) Date of Patent: Feb. 28, 2017

(54) ***CLEMATIS* PLANT NAMED 'EVIPO069'**

(50) Latin Name: *Clematis viticella*
Varietal Denomination: Evipo069

(71) Applicants: Mogens Nyegaard Olesen, Fredensborg (DK); Raymond Evison, St. Sampsons (GG)

(72) Inventors: Mogens Nyegaard Olesen, Fredensborg (DK); Raymond Evison, St. Sampsons (GG)

(73) Assignee: Poulsen Roser A/S, Fredensborg (DK)

( * ) Notice: Subject to any disclaimer, the term of this patent is extended or adjusted under 35 U.S.C. 154(b) by 134 days.

(21) Appl. No.: 14/121,275

(22) Filed: Aug. 15, 2014

(65) Prior Publication Data

US 2016/0050826 P1 Feb. 18, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

"Perfection by Poulsen"—*Clematis*—Main Varieties 2013 (3 pgs).*

* cited by examiner

*Primary Examiner* — Susan McCormick Ewoldt

(57) ABSTRACT

A new *Clematis* plant with a compact growth habit, profuse, red flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

3 Drawing Sheets

Botanical classification: Genus: *Clematis*. Species: *viticella*.

Variety denomination: 'Evipo069'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2001 and the resulting seeds were planted the following winter in a controlled environment in Guernsey, Channel Islands, United Kingdom. The new variety named 'Evipo069' originated as a single seedling from the stated cross.

The new *clematis* plant may be distinguished from its female seed parent and male pollen parent by the following characteristics. The seed parent has deep pink flowers, while the new variety has red flowers. The pollen parent has flowers which have a diameter greater than 150 mm while the new plant has flowers which have a diameter of 100 mm.

The objective of the hybridization of this *clematis* plant was to create a new and distinct variety for nursery culture with unique qualities such as:

1. Uniform and abundant red flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo069' was selected by Mogens N. Olesen and Raymond J. Evison in their *clematis* development program in the Channel Islands, United Kingdom in 2002. Asexual reproduction of 'Evipo069' by means of vegetative cuttings and traditional layering was first performed by Mogens N. Olesen and Raymond J. Evison in the nursery during the summer of 2002. This initial and subsequent asexual propagations have demonstrated that the characteristics of 'Evipo069' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo069'.

Specifically illustrated in FIG. 1 are flower buds, open flower, tepals detached, seed heads, and juvenile growth.

DETAILED DESCRIPTION OF THE VARIETY

Figure 1:
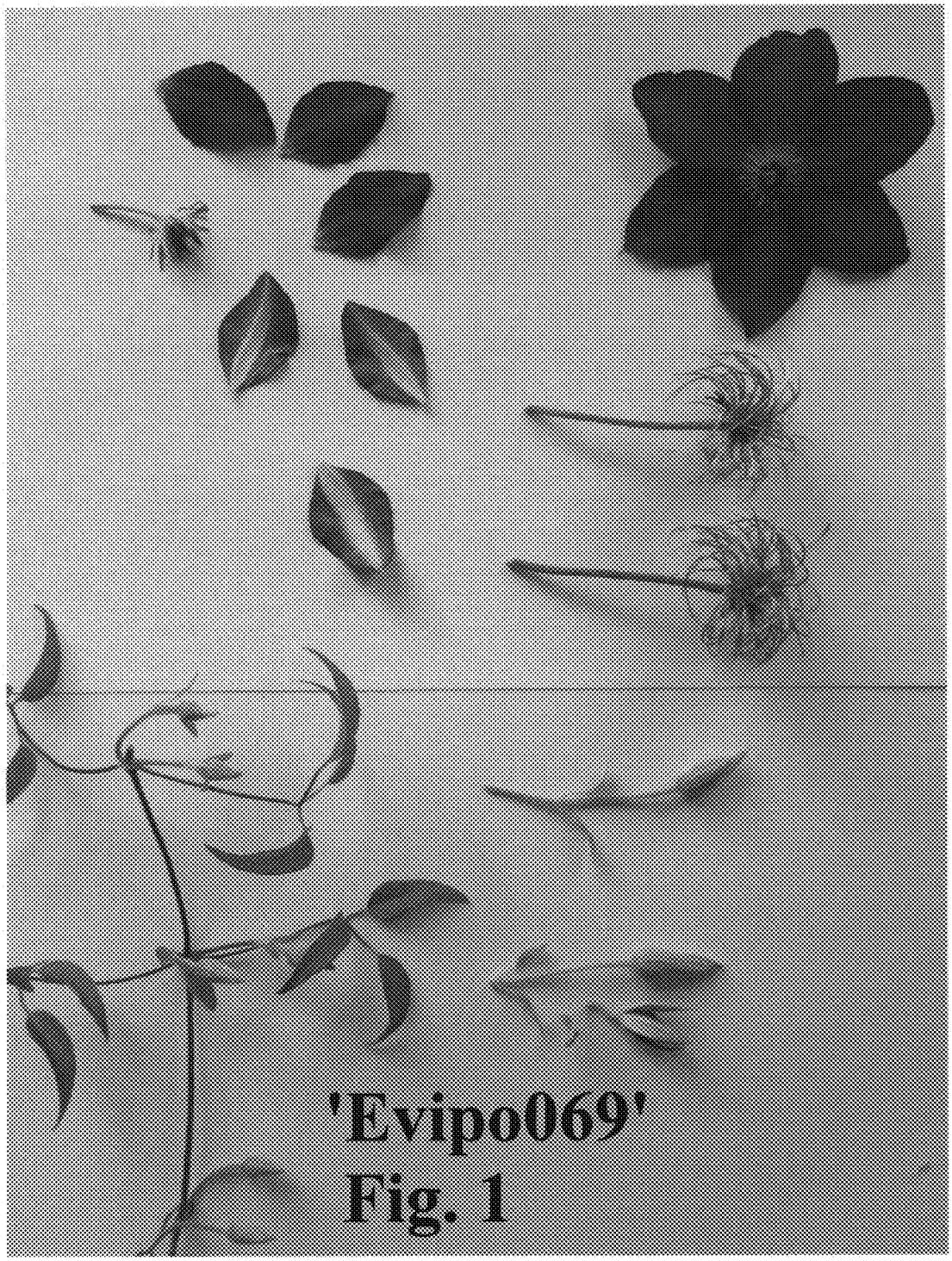
Figure 2:
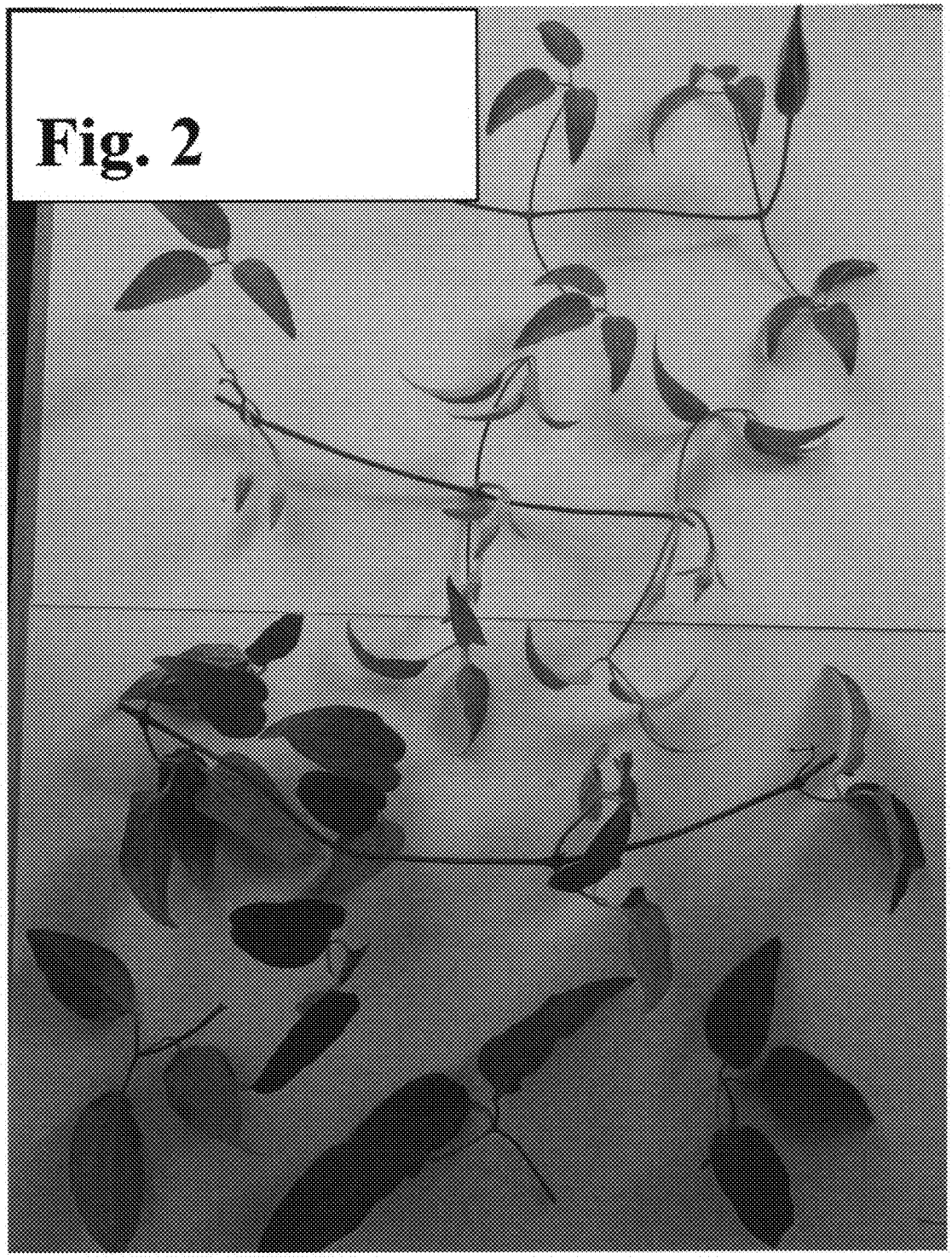
FIG. 2 shows mature and juvenile leaves and stems.
Figure 3:
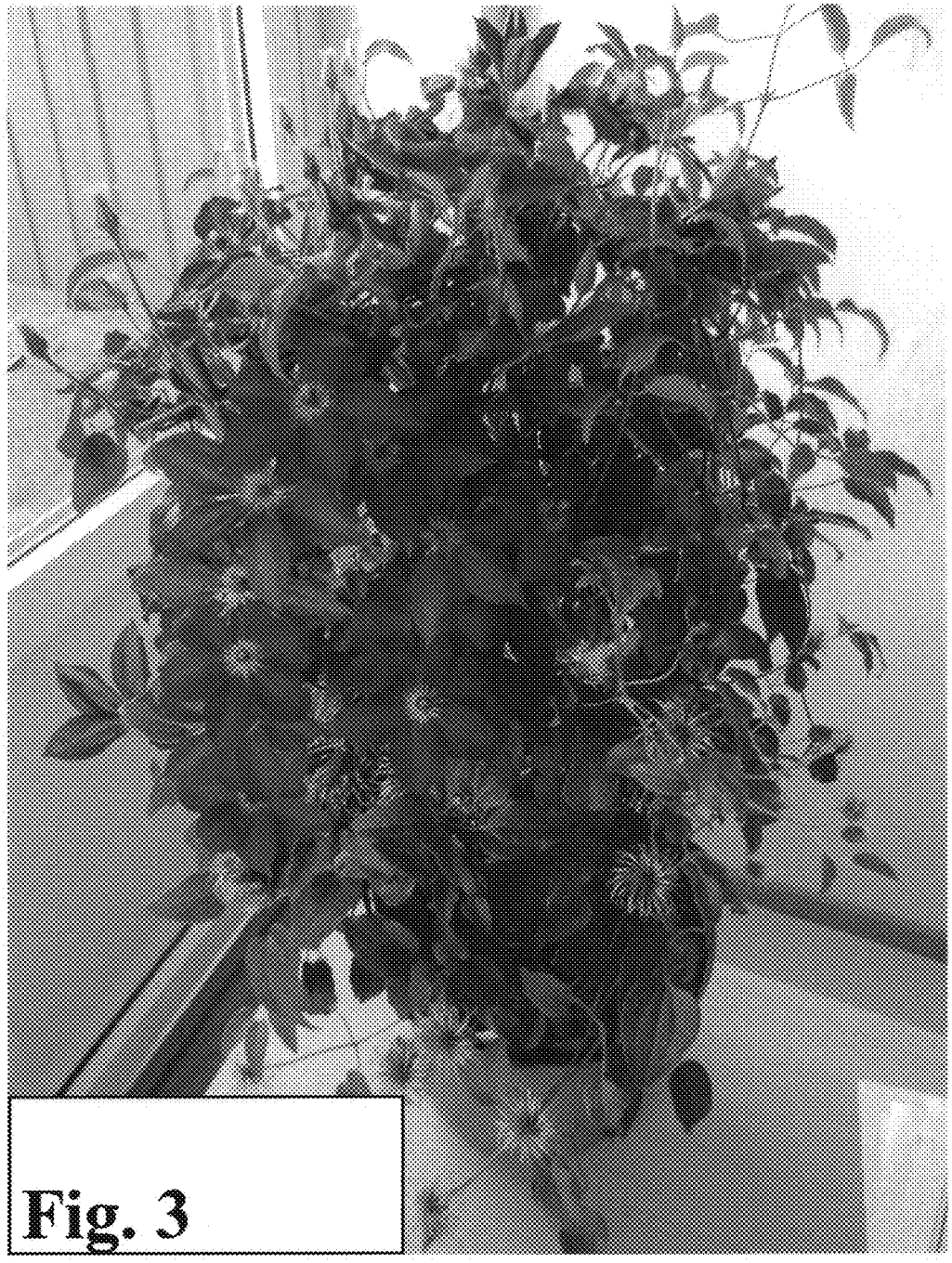
FIG. 3 shows the new variety flowering in a container. Plants shown are 1 year of age.

The following is a detailed description of 'Evipo069', as observed in its growth throughout the flowering period in Fredensborg Denmark. Observed plants were cultivated for a period of 12 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo016' described and illustrated in U.S. Plant Pat. No. 21,583 issued Dec. 21, 2010 are compared to 'Evipo069' in Chart 1.

CHART 1

| | 'Evipo069' | 'Evipo016' |
|---|---|---|
| Flower diameter | 100 mm | 130-185 mm |
| Tepal upper surface after opening | Red-Purple Group 59A | Red Group 53A |
| Anther colour | Violet Group 83A | Grey Orange Group 177A |

Flower and Flower Bud

Blooming habit: Continuous. The natural flowering period is generally from April to September.

Flower bud:
- *Size*.—Normally 30 mm in length. Bud diameter is 10 mm.
- *Bud form*.—Elliptic.
- *Bud color*.—At ¼ opening the flower buds are Yellow-Green Group 144D with intonations of Purple-Violet Group 82B.

Peduncle:
- *Surface texture*.—Lightly pubescent.
- *Length*.—35 to 40 mm.
- *Color*.—Yellow-Green Group 145A.
- *Strength*.—Moderately strong.

Receptacle:
- *Surface texture*.—Smooth.
- *Shape*.—Broad funnel.
- *Size*.—1 mm (h)×3 mm (w).
- *Color*.—Yellow-Green Group 145A.

Flower arrangement:
- *Location on vine*.—New growth only at the shoot apex as well as axillary buds along the stem.
- *Borne*.—Singly and in clusters of 2 flowers.
- *Attitude*.—Mostly upwards, partially horizontal.

Flower bloom:
- *Size*.—On average, flowers are 100 mm in diameter and mm in depth.
- *Profile*.—Open flowers are flat.
- *Fragrance*.—None.
- *Lasting quality*.—Flowers normally remain up to 10 days on the plant.

Tepals:
- *Tepal color*.—Upon opening, the upper surface is Red-Purple Group 59A. The lower surface is Red-Purple Group 59C with a central stripe the color of Yellow-Green Group 145A. After opening, the upper surface is Red-Purple Group 59A. The lower surface is Red-Purple Group 71A with a central stripe the color of Yellow-Green Group 145A.
- *Quantity*.—Normally 6 tepals.
- *Size*.—40 to 45 mm in length by 20 to 30 mm wide.
- *Shape*.—Individual tepal shape is ovate. The tepal apex is acuminate. The tepal base is acute.
- *Apex recurvature*.—Slightly curved.
- *Tepal cross section*.—Slightly cupped.
- *Margins*.—Entire.
- *Persistence*.—Tepals drop off cleanly.
- *Overlap*.—Slightly.

Reproductive organs:
- *Arrangement*.—Moderately open.
- *Pollen*.—None observed.
- *Anthers*.—Size: 4 mm in length. Color: Violet Group 83A. Quantity: On average, 60.
- *Filaments*.—Color: Green-Yellow Group 1D. Length: About 7 mm.
- *Pistils*.—Quantity: On average, 60.
- *Stigmas*.—Superior in location relative to the length of the filaments and the height of the anthers.
- *Styles*.—Color: Green-Yellow Group 1D. Length: About 10 mm.

Seed head characteristics:
- *Size*.—30 mm in height. 40 mm in diameter.
- *Quantity*.—The average number of seeds produced per seed head is 60.
- *Style appearance*.—Plumose, semi-erect.

Plant

Plant form: Climbing and creeping.

Plant growth: Vigorous.

Size: Seasons growth attains 2 to 3 meters in height. Average spread is 250 cm.

Stems:
- *Color*.—Juvenile stems are Greyed-Orange Group 177A. Mature stems are Brown Group 200B.
- *Internodes*.—5 to 10 cm between nodes.
- *Length*.—Normally 50 cm from the base of the plant to the flowering portion of the stem.
- *Diameter*.—Normally 2 mm.
- *Texture*.—Mature stems are generally ribbed.

Plant foliage:
- *Leaf characteristics*.—Deciduous.
- *Arrangement*.—Trifoliate.
- *Leaf size*.—Compound leaves are normally 80 to 100 mm (l)×110 to 150 mm (w). Leaflets are normally 40 to 60 mm (l)×20 to 25 mm (w).
- *Abundance*.—On average 3 leaves per 10 cm of stem.
- *Leaf color*.—Juvenile upper Green Group 140D. Juvenile lower Yellow-Green Group 146B. Mature upper Yellow-Green Group 147A. Mature lower Yellow-Green Group 147B.
- *Stipules*.—Absent.
- *Petioles*.—Size: Normally 20 to 45 mm in length by 1 to 2 mm diameter. Texture: Smooth. Color: Yellow-Green Group 146A.
- *Petioloule*.—Size: Normally 10 to 20 mm in length by 1 mm diameter. Texture: Smooth. Color: Yellow-Green Group 146A.
- *Leaflet shape*.—Generally lanceolate. The base is rounded. The apex is acute.
- *Margin*.—Entire.
- *Surface*.—The upper side is smooth. The lower side is smooth.
- *Thickness*.—Moderate.
- *Glossiness*.—Not. Glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 7.

Heat tolerance: The variety has been found to be suitable for climate conditions found in the American Horticulture Society heat zone 7.

We claim:

1. A new and distinct variety of *clematis* plant named 'Evipo069', substantially as described and illustrated, due to its abundant red flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo069'